US00PP27139P2

(12) United States Plant Patent
Delabroye

(10) Patent No.: US PP27,139 P2
(45) Date of Patent: Sep. 6, 2016

(54) ***HEUCHERA* PLANT NAMED 'APRICOT'**

(50) Latin Name: ***Heuchera* hybrid**
Varietal Denomination: Apricot

(71) Applicant: Thierry Delabroye, Hantay (FR)

(72) Inventor: Thierry Delabroye, Hantay (FR)

(73) Assignee: Sandrine Delabroye, Hantay (FR)

( * ) Notice: Subject to any disclaimer, the term of this patent is extended or adjusted under 35 U.S.C. 154(b) by 115 days.

(21) Appl. No.: 14/120,946

(22) Filed: Jul. 14, 2014

(51) Int. Cl.
*A01H 5/12* (2006.01)

(52) U.S. Cl.
USPC ..... Plt./440

(58) Field of Classification Search
USPC ..... Plt./440
See application file for complete search history.

(56) References Cited

PUBLICATIONS

Vicky & Richard Fox Twitter @Plantagogo, retrieved on Dec. 9, 2015, retrieved from the Internet at <https://twitter.com/plantagogo/status/438229504365170688> one page.*

* cited by examiner

*Primary Examiner* — June Hwu
(74) *Attorney, Agent, or Firm* — Penny J. Aquirre

(57) ABSTRACT

A new cultivar of hybrid *Heuchera* named 'Apricot', characterized by its leaves that are bronze-orange in color, its compact plant habit with a tight mound of foliage, its abundance of flowering stems, and its medium pink flowers on dark red-purple flowering stems.

2 Drawing Sheets

Botanical classification: *Heuchera* hybrid.
Cultivar designation: 'Apricot'.

BACKGROUND OF THE INVENTION

The present invention relates to a new and distinct cultivar of *Heuchera* of hybrid origin, botanically known as a *Heuchera* and is hereinafter referred to by its cultivar name 'Apricot'.

The new cultivar was discovered as a whole plant mutation in a trial field by the Inventor in Hantay, France in June of 2011. The trial field contained hundreds of cultivars and proprietary seedlings of *Heuchera* from the Inventor's breeding program. The parentage of 'Apricot' is therefore unknown.

Asexual propagation of the new cultivar was first accomplished under the direction of the Inventor by in vitro propagation initiated using meristem tissue in Rijswijk, The Netherlands in 2011. Asexual propagation of the new cultivar by stem cuttings and tissue culture has shown that the unique features are stable and reproduced true to type in successive generations.

SUMMARY OF THE INVENTION

The following traits have been repeatedly observed and represent the characteristics of the new cultivar. These attributes in combination distinguish 'Apricot' as a new and unique cultivar of *Heuchera*.

1. 'Apricot' exhibits leaves that are bronze-orange in color.
2. 'Apricot' exhibits a compact plant habit with a tight mound of foliage.
3. 'Apricot' exhibits an abundance of flowering stems.
4. 'Apricot' exhibits medium pink flowers on dark red-purple flowering stems.

'Apricot' can be most closely compared to the *Heuchera* cultivars 'Caramel' (U.S. Plant Pat. No. 16,560) and 'Vulcano' (U.S. Plant Pat. No. 25,625). Both are similar to 'Apricot' in foliage coloration. 'Caramel' differs from 'Apricot' in having leaves that are slightly lighter in color and smaller in size with deeper lobed margins, and in rarely or sparsely producing flowering stems. 'Vulcano' differs from 'Apricot' in having leaves that are lighter in color with more conspicuous veins, flowers that are red in color and in having a shorter plant height.

BRIEF DESCRIPTION OF THE DRAWING

The accompanying colored photographs illustrate the overall appearance and distinct characteristics of the new *Heuchera*. The photographs were taken of a plant one year in age as grown outdoors in a 8.7-liter container in Hillegom, The Netherlands.

The photograph in FIG. 1 provides a side view of the plant habit of 'Apricot' in bloom.

Figure 1:
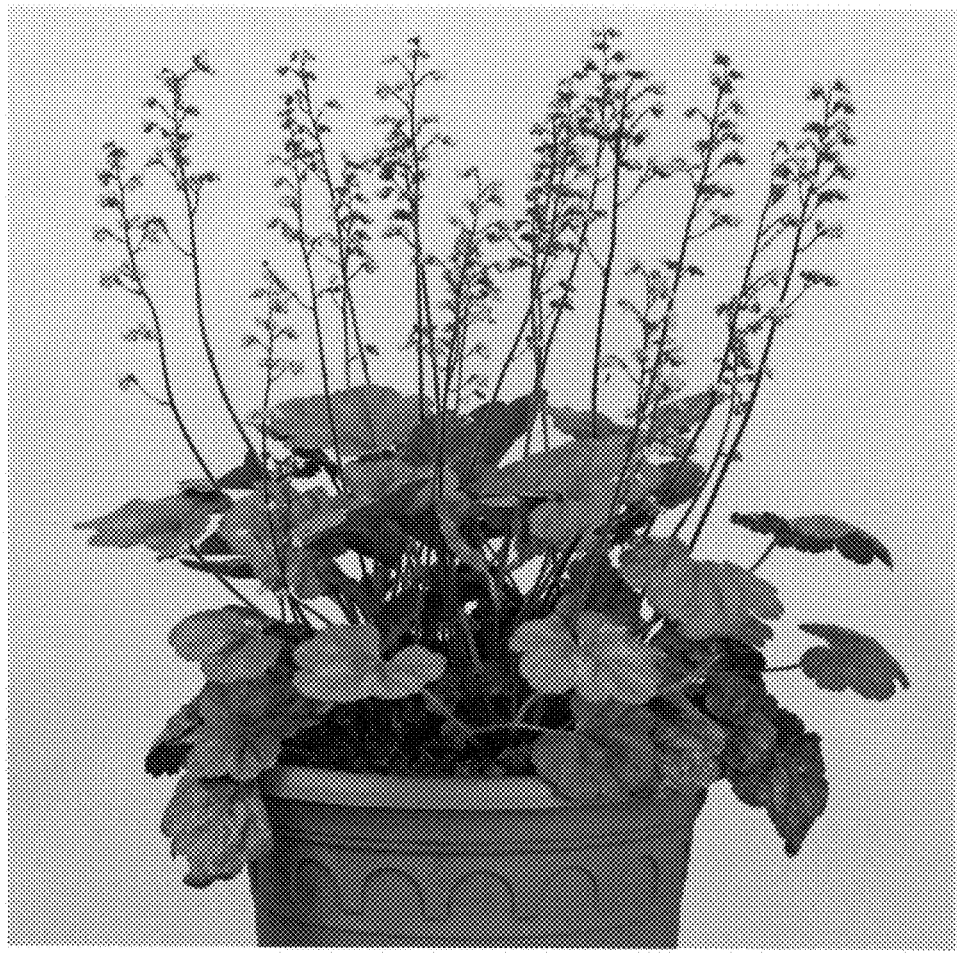
Figure 2:
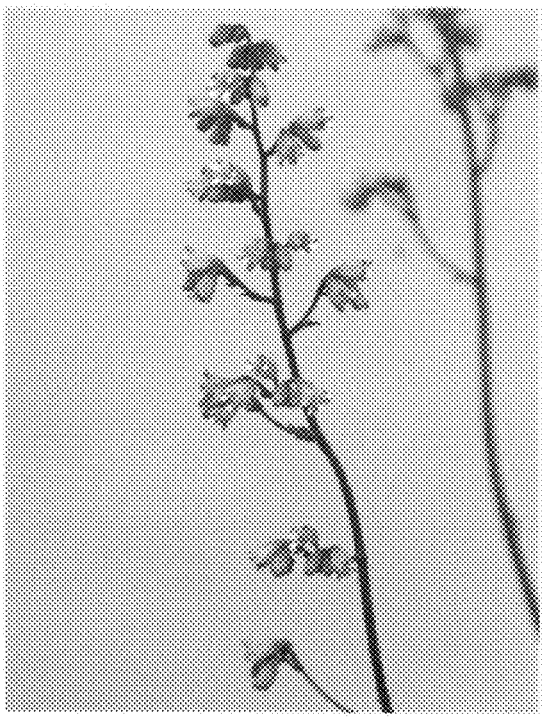

The photograph in FIG. 2 provides a close-up view of the flowers of 'Apricot'.

Figure 3:
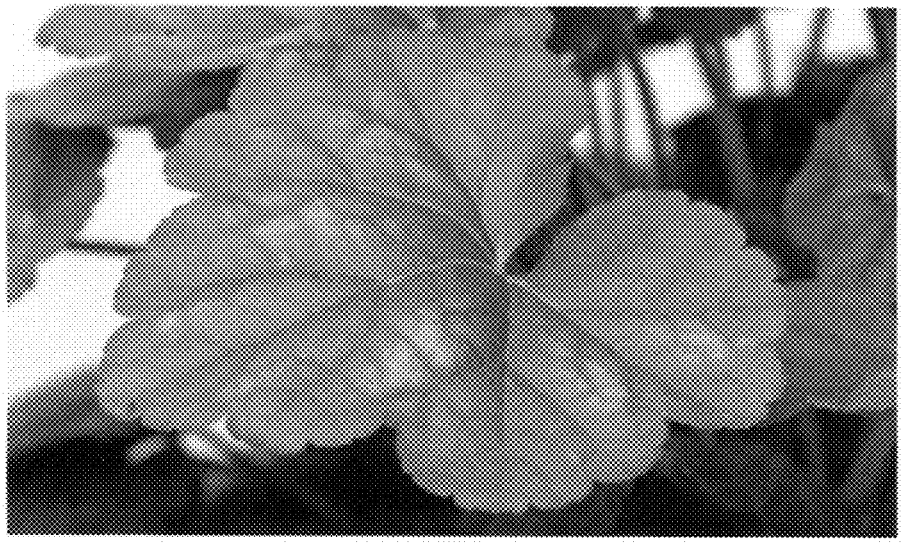

The photograph in FIG. 3 provides a close-up view of a leaf of 'Apricot'.

The colors in the photographs are as close as possible with the digital photography techniques available, the color values cited in the detailed botanical description accurately describe the colors of the new *Heuchera*.

DETAILED BOTANICAL DESCRIPTION OF THE PLANT

The following is a detailed description of 1-year old plants of the new cultivar as grown outdoors in a 8.7-liter container in Hillegom, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Late spring into summer in The Netherlands.

*Plant type*.—Herbaceous perennial.

*Plant habit*.—Compact, clump-forming, mounded foliage.

*Height and spread*.—Average of 19 cm in height from soil to top of leaves and 38 cm from soil to top of inflorescences and 43 cm in width.

*Hardiness*.—At least in U.S.D.A. Zones 3 to 9.

*Diseases and pests*.—Not more susceptible to pests and diseases than other *Heuchera* varieties.

*Environmental stresses*.—Tolerant to heat and humidity.

*Root description*.—Fibrous roots on woody rootstalks.

*Branching habit*.—flowering stem emerge from basal rosettes, no lateral branches.

*Propagation*.—In vitro propagation is the preferred method, stem cuttings and division are also possible.

*Growth rate*.—Moderately vigorous.

Stem description (peduncle, flowering stem):

*Shape*.—Round.

*Stem color*.—A blend of 177A, 177B and 178A.

*Stem size*.—An average of 2 mm in diameter and 35.3 cm in length.

*Stem strength*.—Moderately strong.

*Stem aspect*.—Flowering stems grow in an average angle of 80° to base (0°=horizontal).

*Stem surface*.—Moderately, glossy, densely covered with short hairs, average of 0.05 cm in length, NN155D in color.

*Stem number*.—Average of 56 flowering stems.

Foliage description:

*Leaf shape*.—Orbicular.

*Leaf division*.—Simple.

*Leaf base*.—Hastate, free to slightly overlapping.

*Leaf apex*.—Obtuse.

*Leaf venation*.—Laciniate, upper vein color; young leaves 177D, mature leaves 200A, lower vein color; young leaves 184C, mature leaves N77D.

*Leaf margins*.—Lobed with average of 5 lobes per leaf, lobe margins bi-crenate, lower side margins, main and secondary veins moderately covered with short hairs 1.5 mm in length and NN155D in color.

*Leaf attachment*.—Petiolate.

*Leaf arrangement*.—Alternate, basal rosettes.

*Leaf rugosity*.—Medium.

*Leaf orientation*.—Typically nearly horizontal to petiole and slightly cupped.

*Leaf surface*.—Upper surface very slightly glossy and glabrous, lower side slightly glossy and moderately pubescent on main and secondary veins.

*Leaf color*.—Young upper surface; 176D with slight mottling of 159D between the veins, young lower surface; 183D, mature upper surface; 176D with older leaves (and all leaves in fall) a color between N77C and 201A, mature lower surface; 184B with older leaves (and all leaves in fall) N77D.

*Leaf size*.—Average of 8.8 cm in length and 8.7 cm in width.

*Leaf quantity*.—17 per basal rosette.

*Petioles*.—Average of 14.4 cm in length and 2.5 mm in width, color 181B to 181C, older petioles 177B, surface covered with dense soft pubescence, average of 2.5 mm in length and 155A in color.

*Stipules*.—Small leafy stipules at the base of each leaf, narrow acute apex, with an average of 1.8 cm in length and 3 mm in width, color; 68D, base 60D.

Flower description:

*Inflorescence type*.—Numerous small bell-shaped flowers arranged on pyramidal panicles on flower scapes emerging from the base of the rosette.

*Inflorescence size*.—An average of 12.7 cm in height (excluding peduncle) and 5.2 cm in width.

*Inflorescence number*.—An average of 56 per 8.7-liter container.

*Flower fragrance*.—None.

*Flower quantity*.—Average of 152 flowers per flowering stem.

*Flower lastingness*.—Average of one week.

*Flower buds*.—Oblong in shape, an average of 5 mm in diameter and 2.5 mm in diameter, 61C in color.

*Flower aspect*.—Outward to slightly nodding.

*Flower type*.—Campanulate.

*Flower size*.—About 7 mm in length and 6 mm in diameter.

*Petals*.—About 5, rotate arrangement and implanted in the hypanthium at base, oblanceolate in shape, margin is entire, apex is narrowly acute, upper and lower surface is matte and glabrous, color of upper and lower surface when opening; 70D, color of upper and lower surface when fully open; 69C, base 70D, about 4 mm in length and 1 mm in width.

*Calyx*.—Campanulate, sepals fused to hypanthium, 6 mm in length and 5 mm in diameter.

*Sepals*.—5, fused, campanulate hypanthium, oblong in shape, about 6 mm in length and 2 mm in width, margin is entire, apex is obtuse, fused base, surfaces are matte, lower side is moderately covered with very short glandular hairs 0.025 cm in length and between N155B and 69D in color, color: immature upper surface; 59D, immature lower surface; between 61D and 62A, base 61D, mature upper surface; 59D, heavily flushed 147D, margins 59D, mature lower surface; 61D, base 53C.

*Bracts*.—1, at base of petioles, lanceolate in shape, 178A in color, about 2 mm in length and 0.7 mm in width, acute apex, base truncate.

*Pedicels*.—Average of 3.5 mm in length and 0.5 mm in width, 178A in color, moderate strength, average angle of 35° (0°=straight on top of secondary peduncle).

Reproductive organs:

*Gynoecium*.—2 pistils, 3 mm in length, stigma is pointed in shape, 157A in color, styles are 2.5 mm in length and 157D in color, ovaries are 146D in color.

*Androcoecium*.—About 5 stamens, anthers are ovate in shape, about 0.5 mm in length and 24B in color, filament 3.5 mm in length and 69C to 69D in color, pollen is low in quantity and 22A in color.

*Seed/fruit*.—No fruit or seeds were observed.

It is claimed:

1. A new and distinct cultivar of hybrid *Heuchera* plant named 'Apricot' as herein illustrated and described.

* * * * *